(12) United States Patent
Harrison

(10) Patent No.: US 12,313,451 B2
(45) Date of Patent: May 27, 2025

(54) FINGER WEARABLE LIGHT METER

(71) Applicant: KORRUS, INC., Los Angeles, CA (US)

(72) Inventor: Benjamin Harrison, Los Angeles, CA (US)

(73) Assignee: Korrus, Inc., Los Angeles, CA (US)

( * ) Notice: Subject to any disclaimer, the term of this patent is extended or adjusted under 35 U.S.C. 154(b) by 425 days.

(21) Appl. No.: 17/729,757

(22) Filed: Apr. 26, 2022

(65) Prior Publication Data

US 2022/0341777 A1    Oct. 27, 2022

Related U.S. Application Data

(60) Provisional application No. 63/179,835, filed on Apr. 26, 2021.

(51) Int. Cl.
| | |
|---|---|
| *G01J 1/02* | (2006.01) |
| *G01J 1/16* | (2006.01) |
| *G01J 1/42* | (2006.01) |
| *G01J 3/36* | (2006.01) |
| *G01J 5/02* | (2022.01) |
| *G01J 5/10* | (2006.01) |
| *G08B 21/18* | (2006.01) |

(52) U.S. Cl.
CPC ........... *G01J 1/0233* (2013.01); *G01J 1/0271* (2013.01); *G01J 1/16* (2013.01); *G01J 1/42* (2013.01); *G01J 1/4204* (2013.01); *G01J 3/36* (2013.01); *G01J 5/0265* (2013.01); *G01J 5/10* (2013.01); *G08B 21/182* (2013.01); *G01J 2001/0257* (2013.01)

(58) Field of Classification Search
CPC .......... G01J 1/02; G01J 1/0204; G01J 1/0233; G01J 2001/0257; G01J 1/0271; G01J 1/16; G01J 1/42; G01J 3/28; G01J 3/2803; G01J 3/30; G01J 3/36; G01J 3/50; G01J 5/02; G01J 5/0265; G01J 5/04; G01J 5/08; G01J 5/0801; G01J 5/0846; G01J 5/10
USPC ........ 250/336.1, 338.1, 338.4, 339.05, 341.8
See application file for complete search history.

(56) References Cited

U.S. PATENT DOCUMENTS

| | | | |
|---|---|---|---|
| 9,582,034 B2 * | 2/2017 | von Badinski | A61B 5/332 |
| 9,592,007 B2 * | 3/2017 | Nuovo | A61B 5/318 |
| 10,307,101 B1 * | 6/2019 | Miller | A61B 5/0059 |
| 10,559,220 B2 * | 2/2020 | Wisbey | G16H 50/30 |
| 10,918,289 B1 * | 2/2021 | Wasson | A61B 5/0022 |
| 11,099,064 B2 * | 8/2021 | Matthys | G01J 1/0403 |

* cited by examiner

*Primary Examiner* — Allen C. Ho
(74) *Attorney, Agent, or Firm* — FisherBroyles LLP

(57) ABSTRACT

A method includes sensing data indicative of a plurality of wavelengths of light utilizing one or more sensors forming a part of a sensor ring, storing the data on a memory device forming a part of the sensor ring, transmitting the data to a computing device external to the ring and receiving a photic environmental model from the computing device the photic environmental model based, at least in part, on the data.

6 Claims, 3 Drawing Sheets

FINGER WEARABLE LIGHT METER

CROSS REFERENCE TO RELATED APPLICATIONS

This application claims the benefit of U.S. Provisional Patent Application 63/179,835, filed Apr. 26, 2021, the entire disclosure of which is hereby incorporated herein by reference.

TECHNICAL FIELD

The present disclosure relates generally to systems and methods for measuring light exposure.

BACKGROUND

In order to optimize an individual's photic zeitgeber, it is necessary to measure and track their actual light exposure. Existing devices today for this are watches, clip-ons, necklaces, or spectacles. These all have issues that decrease their ability to collect useful data. Watches are frequently obscured by clothing, e.g., shirt sleeves. Clip-ons and necklaces are easily forgotten or may be covered by clothing, e.g., an overcoat. Spectacles are somewhat intrusive if they are not worn anyway and adding a sensor to prescription spectacles is costly and inconvenient.

There exists, therefore, a need for a light sensor that overcomes the problems in the existing and prior art.

SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

In accordance with an exemplary and non-limiting embodiment, a method comprises sensing data indicative of a plurality of wavelengths of light utilizing one or more sensors forming a part of a sensor ring, storing the data on a memory device forming a part of the sensor ring, transmitting the data to a computing device external to the ring and receiving a photic environmental model from the computing device the photic environmental model based, at least in part, on the data.

DETAILED DESCRIPTION

Figure 1:
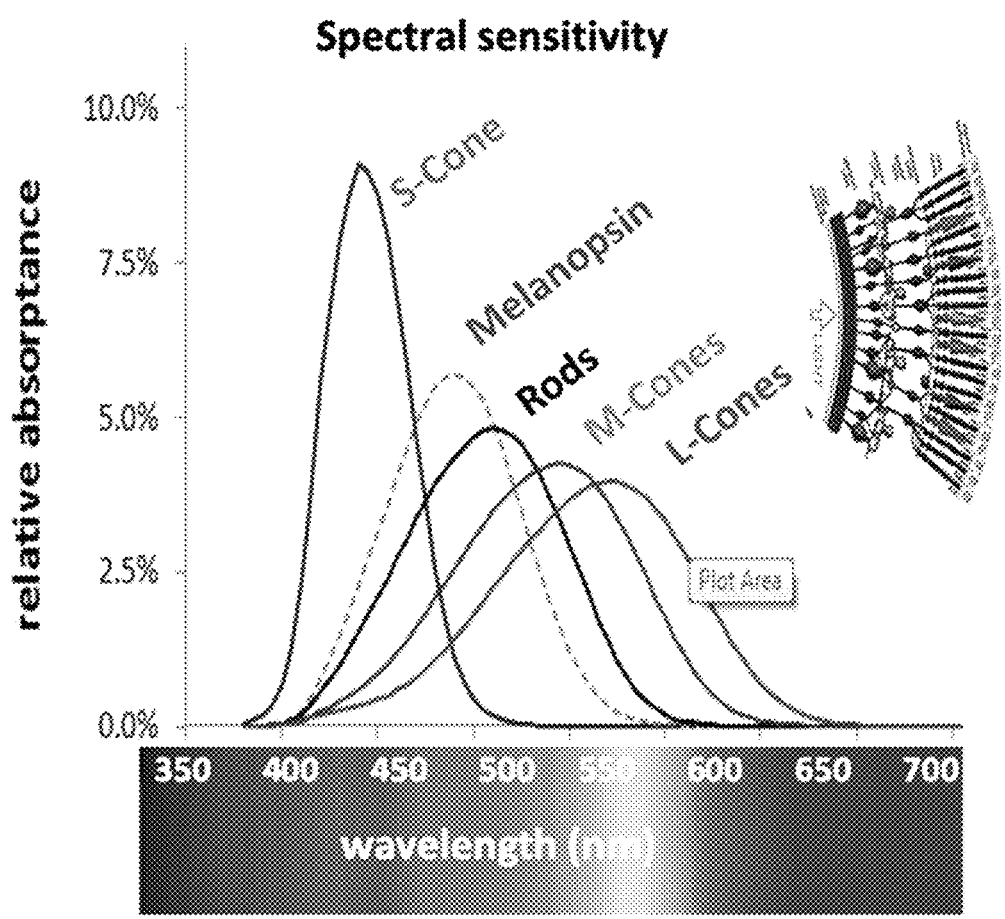
FIG. 1 illustrates the spectral sensitivity of various structures of the human eye.

As used throughout this application, the word "may" is used in a permissive sense (i.e., meaning having the potential to), rather than the mandatory sense (i.e., meaning must). The words "include," "including," and "includes" and the like mean including, but not limited to. As used herein, the singular form of "a," "an," and "the" include plural references unless the context clearly dictates otherwise. As employed herein, the term "number" shall mean one or an integer greater than one (i.e., a plurality).

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

These drawings may not be drawn to scale and may not precisely reflect structure or performance characteristics of any given exemplary implementation, and should not be interpreted as defining or limiting the range of values or properties encompassed by exemplary implementations.

Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device.

This disclosure includes a non-limiting set of embodiments used to describe certain inventions.

In most cases, fingers are exposed to the world, so enabling photic measurements.

In accordance with exemplary and non-limiting embodiments a wearable, electronic ring features a light sensor. This ring may communicate with an external system. The ring may optionally store and process light information on board. It may share this processed data. It may also share raw data. The ring may optionally include additional sensors, e.g., accelerometers, gyroscopes, optical heartrate monitors, thermometers, pulse oximetry, microfluidic sweat sensors, galvanic skin response.

The light sensor may be a single sensor with a sensitivity curve, the light sensor may comprise multiple sensors with multiple sensitivity curves, or it may be a spectrometer. Examples of sensitivities are 1. Photopic
2. Scotopic
3. Melanopic (~480 nm)
4. Chloropic (~530 nm)
5. Rhodopic (~496 nm)
6. Erythropic (~558 nm)
7. Cyanopic (~419 nm)
8. nUV (300-400 nm)
9. NIR (700-1100 nm)

FIG. 1 is an illustration of the sensitivity of various anatomical structures involved in the human perception of light.

In accordance with exemplary embodiments, a spectrometer may, for example, have sensitivity from 360 nm to 780 nm, with 5 nm bins. Sensitivity for the sensors may range, for example, between 0.001 lux and 200,000 lux. In some embodiments, onboard processing may be employed, for example, to combine input from sensor types 3-7 to produce a single circadian metric, e.g., circadian stimulus.

Figure 2:
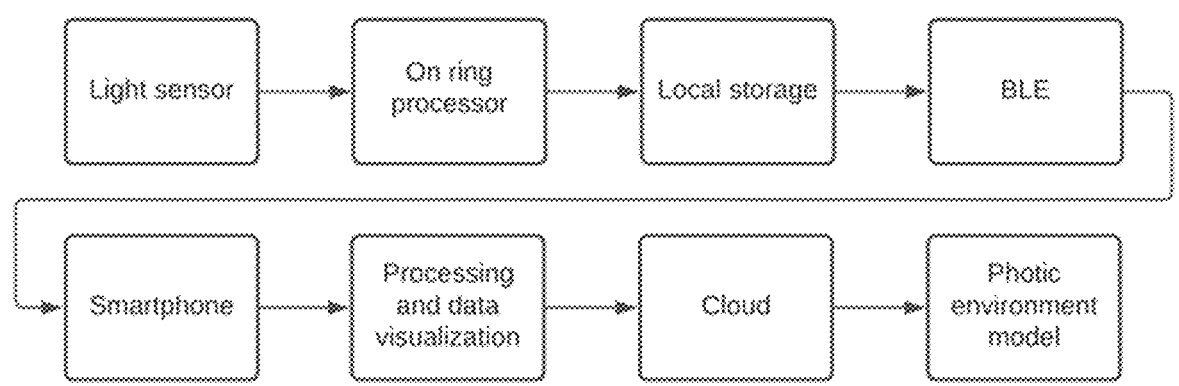
FIG. 2 illustrates a flow chart in accordance with the principles of the present invention.

With reference to FIG. 2, there is illustrated an exemplary and non-limiting embodiment of a flowchart showing the operation of the wearable light meter as may be embodied in a ring.

As shown, data indicative of various wavelengths of light present in an environment may be sensed by a light meter forming a part of the ring. This light sensor data may then be processed by one or more processors forming a part of the ring. The results of the processing, as well as raw data collected by the light sensor of light sensors, may then be committed to local storage forming a part of the ring. Then data stored in local storage may be communicated to an entity external to the ring via, for example, Bluetooth Low Energy (BLE) technology and/or Bluetooth communication. As illustrated, local storage data is wirelessly communicated to a smartphone which may perform further processing and data visualization upon the data. The results of the processing and data visualization may be stored in the cloud and/or may be utilized to produce a photic environment model indicative of the environment in which wearable light meter is operating.

Figure 3:
FIG. 3 illustrates an exemplary and non-limiting embodiment of a sensor ring.

With reference to FIG. 3, there is illustrated an exemplary and non-limiting embodiment of a sensor ring 300. As discussed above, sensor ring 300 may be formed of one or more light sensors 302 in communication with a processor 304 and a memory 306. Sensor ring 300 may further incorporate communication hardware and software sufficient to enable the communication to external entities and the receipt of information and data from outside entities. In other embodiments, sensor ring 300 may further provide visual, audio and/or tactile feedback to a wearer of the ring. This may be accomplished, for example, via embedded LED lights, speakers, vibrating elements and the like.

In some embodiments, the sensor ring 300 may operate to utilize received data to influence the actions of a wearer of the sensor ring 300. For example, the photic environment model indicative of the environment in which wearable light meter is operating may be utilized to improve the health of the wearer. In one example, there may be stored a profile of the wearer storing preferred lighting requirements of the wearer. A user may, for example, prefer a certain amount of exposure to a certain wavelength profile for a certain amount of time over the course of a day in order to maintain circadian rhythms. A processor, either in the sensor ring 300, external to the sensor ring, and/or operating in the cloud may compare data acquired from the sensor ring 300 with the stored wearer preferences and other external sources of data.

For example, it may be determined that the wearer has been in an environment with an insufficient amount of blue wavelength light for an extended period of time and, as a result, the wearers circadian rhythm is likely to be adversely affected. As a result, the ring may emit a color and/or a tone or vibrate so as to alert the wearer to the situation. In some embodiments, the alert so generated is produced in coordination with data appearing on the smartphone. For example, upon sensing the generated alert, the wearer may consult his smartphone to receive information indicating that he should head outdoors or find another source of daylight. Upon doing so, software operating on one or more processors in the ring 300, the smartphone, the cloud or elsewhere may work, either singularly or in concert, to analyze the sensor signal obtained by the ring to ensure that the wearer is now receiving an appropriate light profile.

In other embodiments, one or more processors may analyze the data from the light sensors to determine if the wearer has received a harmful dose of light of a particular wavelength range. In such an instance, the ring may alert the wearer to retire to an appropriate environment free of the harmful light.

In other embodiments, the sensor ring 300 may inform the wearer when a light goal is achieved. For example, a wearer may store a predetermined light profile or light goal to be achieved on a daily basis a weekly basis and the like. When the sensor ring 300 sensors detect a light absorption profile that fulfills the goals of the light profile, the ring may vibrate and/or flash lights and/or emit a sound indicative of the attainment of the goal. In this manner, a wearer may be informed that he/she has received a desired amount and quality of light.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the invention has been explained in relation to its preferred embodiment, it is to be understood that many other possible modifications and variations can be made without departing from the spirit and scope of the invention.

What is claimed is:

1. A method comprising:
    sensing data indicative of a plurality of wavelengths of light utilizing one or more sensors forming a part of a sensor ring;
    storing the data on a memory device forming a part of the sensor ring;
    transmitting the data to a computing device external to the sensor ring; and
    receiving a photic environmental model from the computing device, the photic environmental model based, at least in part, on the data.

2. The method of claim 1, further comprising activating an alert selected from the group consisting of a visual alert, an audio alert, and a tactile alert.

3. The method of claim 2, wherein the alert is activated in response to a comparison of the photic environmental model to a preference of a wearer of the sensor ring.

4. The method of claim 3, wherein the preference of the wearer of the sensor ring is defined by the wearer of the sensor ring.

5. The method of claim 2, wherein the alert indicates to a wearer of the sensor ring that additional information is available on the computing device.

6. The method of claim 5, wherein the computing device is a smartphone.

* * * * *